United States Patent
Crich et al.

(10) Patent No.: US 6,849,767 B2
(45) Date of Patent: Feb. 1, 2005

(54) METHOD OF HYDROBORATING ALCOHOLS AND REDUCING FUNCTIONAL GROUPS USING A RECYCLABLE FLUOROUS BORANE-SULFIDE

(75) Inventors: David C. Crich, Chicago, IL (US); Santhosh Neelamkavil, Philadelphia, PA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 10/625,982

(22) Filed: Jul. 24, 2003

(65) Prior Publication Data

US 2004/0116747 A1 Jun. 17, 2004

Related U.S. Application Data

(60) Provisional application No. 60/398,414, filed on Jul. 25, 2002.

(51) Int. Cl.$^7$ .............................................. C07C 5/02
(52) U.S. Cl. .................. 568/6; 536/18.1; 548/429; 564/375; 564/391; 568/705; 568/814; 568/820; 568/832; 568/880; 568/910
(58) Field of Search ......................... 568/6, 705, 814, 568/820, 832, 880, 910, 1, 38; 536/18.1; 548/429; 564/375, 391

(56) References Cited

U.S. PATENT DOCUMENTS

| | | | |
|---|---|---|---|
| 3,476,812 A | | 11/1969 | Terrell |
| 5,171,736 A | * | 12/1992 | Seyferth et al. .......... 501/196.2 |
| 5,567,849 A | * | 10/1996 | Brown .......................... 568/6 |

OTHER PUBLICATIONS

Organic Letters by Crich and Neelamkavil vol. 4, No. 23 pp. 4175–4177 Oct. 2002.*

CA:133:335260 abs of J Organic Chem by Zaidlewicz et al 65(20) pp 6697–6702 2000.*

D. Crich et al., *Organic Letters* 4(23), 4175–4177 (2002).

D. Crich et al., *Tetrahedron, vol. 58*, No. 20, 3865–3870 (2002).

* cited by examiner

*Primary Examiner*—Michael L. Shippen
(74) *Attorney, Agent, or Firm*—Marshall, Gerstein & Borun LLP

(57) ABSTRACT

A method of hydroborating an alkene or alkyne, or reducing an organic functionality, oxidizing primary and secondary alcohols using a fluorous borane-sulfide is disclosed. The method includes regeneration and recycling the fluorous borane-sulfide.

24 Claims, No Drawings

METHOD OF HYDROBORATING ALCOHOLS AND REDUCING FUNCTIONAL GROUPS USING A RECYCLABLE FLUOROUS BORANE-SULFIDE

CROSS REFERENCE TO RELATED APPLICATION

This application claims the benefit of U.S. provisional patent application Ser. No. 60/398,414, filed Jul. 25, 2002.

STATEMENT OF GOVERNMENTAL INTEREST

This invention was made with government support under CHE 9986200 awarded by the National Science Foundation.

FIELD OF THE INVENTION

The present invention relates to fluorous borane-sulfides and to facile and environmentally acceptable methods of hydroborating alkenes and alkynes and of reducing various organic functional groups. More particularly, the present invention relates to the hydroboration of alkenes and alkynes and to the reduction of functional groups using a recyclable, fluorous borane-sulfide.

BACKGROUND OF THE INVENTION

Borane is one of the most useful and widely used organic reagents. Borane enables the hydroboration of alkenes and alkynes, and a myriad of chemical transformations arising from the so-formed organoborane derivatives. Borane also enables reductions of a host of other organic functionalities. The instability and low reactivity of diborane toward alkenes has resulted in the development of numerous more reactive borane complexes. In addition, the pyrophoric nature of borane renders both its use and transportation hazardous. Therefore, borane typically is coordinated, e.g., to tetrahydrofuran ($BH_3 \cdot THF$)[1,2] or dimethyl sulfide ($BH_3 \cdot SMe_2$, i.e., BMS)[3-6], with BMS being preferred because of its greater stability.

The hydroboration of alkenes and the reduction of numerous organic functional groups by borane-dimethyl sulfide (BMS) are extremely common transformations in organic synthesis.[2-4] This includes the use of BMS as a relatively stable borane carrier for the generation of chiral boranes, such as diisopinocampheylborane, β-isopinocampheyl-9-borabicyclo[3.3.1]nonane, and other such chiral boranes.[5] It also includes the use of BMS to generate the active species from chiral oxaborolidine precatalysts for use in asymmetric reductions.[29] BMS, therefore, is extremely widely used in academic and industrial laboratories, but much less so in industrial processes.

Although BMS is considerably more practical to use than borane itself, BMS suffers from the disadvantage of liberating stoichiometric amounts of dimethyl sulfide in the course of its reactions. Dimethyl sulfide is an extremely volatile (b.p. 37° C.) and foul-smelling compound. The generation of dimethyl sulfide also is environmentally unacceptable, which makes BMS-mediated reactions undesirable for large commercial applications. For example, if used in a large reaction scale, a BMS mediated reaction would require scrubbing of the waste stream. BMS also has stability problems and is pyrophoric.

These disadvantages enormously restrict the use of BMS on an industrial scale. Attempts to overcome these problems include the use of water-soluble sulfides and nonvolatile sulfides,[8,9] but these approaches are deficient in terms of recyclability of the sulfide. Also, see H. C. Brown et al., *J. Org. Chem.*, 51, pp. 4970–4976 (1992).

For example, the disadvantages of BMS prompted investigators to use 1,4-thioxane[7] as a less volatile carrier for borane, and, more recently, bis(hydroxyethyl) sulfide,[8] which has the additional advantage of being water soluble, and therefore is conveniently removed by aqueous extraction following reductions using $BH_3 \cdot S(CH_2CH_2OH)_2$. Other sulfides that have been used as carriers for borane include 1,2-bis(tert-butylthio)ethane and 1,4-bis(benzylthio) butane.[9]

The present invention, therefore, is directed to improved methods of hydroborating alkenes and alkynes and of reducing various organic functionalities using borane in a large scale, and that overcome the disadvantages associated with prior synthetic methods using a borane-sulfide complex. The present invention particularly is directed to using 2-(perfluorooctyl)ethyl methyl sulfide and similar fluorous sulfides as readily prepared, odorless, nonflammable sulfides for complexation and stabilization of borane. The fluorinated sulfides also are readily recycled.

SUMMARY OF THE INVENTION

The commercial, environmentally friendly hydroboration of alkenes and alkynes, and the reduction of various organic functional groups using borane, have been hindered because of the disadvantages and problems associated with using uncomplexed borane or the generation of noxious by-products from borane complexes, such as dimethyl sulfide from BMS. Therefore, the present invention is directed to commercial scale methods of hydroborating alkenes and alkynes, and of reducing organic functionalities, using a borane complex that overcomes the environmental and disposal problems associated with prior borane-mediated methods.

In particular, the present invention is directed to a methods of hydroborating alkenes and alkynes, and of reducing other organic functionalities, using a fluorous borane-sulfide to overcome problems associated with BMS and other sulfide-complexed boranes used in prior methods.

As demonstrated hereafter, the present invention enables all current applications of BMS to be conducted in a facile, safe, odorless manner. Thus, a mixture of a fluorous sulfide and a fluorous borane-sulfide, either as a solid, a suspension in a fluorinated solvent, or a solution in a suitable organic solvent, such as dichloromethane, THF, or benzotrifluoride, are direct replacements for BMS, but with greatly reduced environmental and toxicological hazards and odor. The present invention also has significant environmental and economic advantages because the spent fluorous borane-sulfide, enriched in the fluorous sulfide, can be recycled by contact with borane gas. Therefore, the discharge of sulfides, either water soluble or water insoluble, to the environment is minimized.

The improved hydroboration reaction is important because of the wide scope of the reaction with respect to preparing alcohols and other organic compounds, and its potential use on an industrial scale. An important feature of the present invention is to provide an improved hydroboration reaction that avoids the generation of environmentally unfriendly dimethyl sulfide, while maintaining the ease and broad scope of BMS reactions. An additional advantage would be use of a borane complex that can be quickly regenerated and recycled into the hydroboration or other reduction reactions.

Accordingly, the present invention is directed to a modified hydroboration reaction wherein a fluorous borane-sulfide complex is substituted for the BMS complex. In particular, one aspect of the present invention is to provide a fluorous borane-sulfide that overcomes the disadvantages associated with BMS and other complexing agents for borane. The fluorous borane-sulfide has a general structural formula (I)

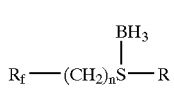

(I)

wherein $R_f$ is a fluorinated hydrocarbon chain containing one to twelve carbon atoms; R is $C_{1-4}$alkyl or $(CH_2)_n$—$R_f$; and n is an integer 1 to 3.

Another aspect of the present invention is to provide a fluorous borane-sulfide of structural formula (I) wherein $R_f$ contains four to ten carbon atoms and, preferably, is perfluorinated; R is $C_{1-4}$alkyl, preferably, methyl or ethyl; and n is 2.

Another aspect of the present invention is to provide a fluorous borane-sulfide that avoids the stoichiometric generation of environmentally unfriendly dimethyl sulfide, incorporates a single, relatively short perfluoroalkyl chain (e.g., four to eight carbon atoms), is soluble or dispersible in organic and fluorinated solvents, and is economical and easy to synthesize.

Yet another aspect of the present invention is to provide a method of hydroborating an alkene or an alkyne, and a method of reducing organic functionalities, like ketones, nitriles, amides, and esters, using a fluorous borane-sulfide of structural formula (I).

Still another aspect of the present invention is to provide a method of regenerating and recycling the fluorous borane-sulfide of structural formula (I) by borating a fluorous sulfide of structural formula $R_f$—$(CH_2)_n$—S—R generated in the hydroboration reaction to regenerate the fluorous borane-sulfide of structural formula (I).

Another aspect of the present invention is to provide a facile preparation of a viscous, odor-free fluorous sulfide, e.g., 3,3,4,4,5,5,6,6,7,7,-8,8,9,9,10,10,10-heptadecafluorodecyl methyl sulfide, its complex with borane, i.e., fluorous BMS, and its higher and lower homologs. In another aspect, the invention further provides the use of a fluorous borane-sulfide of structural formula (I) in hydroboration reactions and in the reduction of numerous other organic functional groups, and its regeneration and recycling.

These and other novel aspects and advantages of the present invention will become apparent from the following detailed description of the preferred embodiments.

DETAILED DESCRIPTION OF THE PREFERRED EMBODIMENTS

The present invention is directed to improved methods for the facile commercial hydroboration of alkenes and alkynes, and the reduction of various organic functionalities using borane. The reactions utilize a fluorous borane-sulfide that overcomes the problems associated with BMS and similar borane complexes utilized in prior hydroboration and borane reduction reactions.

The present invention, therefore, is directed to readily regenerated and recycled fluorous borane-sulfides useful in hydroboration and reduction reactions. Using a virgin or a recycled fluorous borane-sulfide of structural formula (I) retains all the desirable properties of the hydroboration and reduction reactions, while overcoming the problems associated with borane-BMS and other hydroborating complexes.

The fluorous borane-sulfides useful in the present invention have a structural formula (I)

(I)

wherein $R_f$ is a fluorinated hydrocarbon chain having one to twelve carbon atoms; R is $C_{1-4}$alkyl or $(CH_2)_n$—$R_f$; and n is an integer 1 to 3.

An important feature of the fluorous borane-sulfides (I), and the present hydroboration and reduction methods, is regeneration and recycling of the fluorous borane-sulfide. The recycling process optionally includes an extraction step using a perfluorinated hydrocarbon solvent, and includes a borating step using $BH_3$. Perfluorohydrocarbons, also termed fluorous hydrocarbons, are produced industrially on a large scale. They are immiscible with both common organic solvents and water. Organic chemical moieties linked to a perfluorohydrocarbon chain of sufficient size are extracted from an organic solvent into a fluorous hydrocarbon, thereby allowing their ready recovery and recycling. See A. Studer et al., *Science*, 275, pp. 823–826 (1997); I. T. Horvath, *Acc. Chem. Res.*, 31, pp. 641–650 (1998); and D. P. Curran, *Angew. Chem. Int. Ed. Engl.*, 37, pp. 1174–1196 (1998). Fluorous compounds also can be separated from standard organic solvents by preferential retention on a fluorous silica gel followed by subsequent elution with a fluorous solvent. See Q. Zhang et al., *J. Org. Chem.* 65, pp. 8866–8873 (2000).

The fluorous borane-sulfides of structural formula (I) require a sufficient amount of fluorine for solubilization or dispersion in a perfluorinated solvent. In accordance with an important feature of the present invention, a fluorous borane-sulfide requires at least 35% fluorine by weight, and preferably at least about 38% fluorine, by weight, of the fluorous sulfide. In general, the fluorous borane-sulfide contains at least 35% to about 70%, and preferably about 40% to about 65%, by weight of the fluorous sulfide, fluorine. To achieve the full advantage of the present invention, the fluorous borane-sulfide contains about 45% to about 65%, by weight of the fluorous sulfide, fluorine.

The weight percent fluorine in the fluorous borane-sulfide is determined by the length of the $R_f$ chain or chains, and the amount of fluorine in the $R_f$ chain or chains. If the fluorous borane-sulfide contains two $R_f$ groups, the $R_f$ groups can be the same or different.

Another important feature of the present invention is the length of the spacer linking the fluorinated alkyl chain to the S—$BH_3$ moiety of the fluorous sulfide. Fluorous-borane sulfides lacking a spacer, i.e., having a fluorinated alkyl chain bound directly to the S—R moiety (i.e., n=0), are unsuitable because the nucleophilicity of the fluorous sulfide is reduced, and, therefore, have a disadvantage of reduced adhesion to borane. A linker having one methylene group (i.e., n=1) is useful, but has a disadvantage of eliminating hydrogen fluoride (HF) from the sulfide. A linker having three methylene groups also is effective, but requires a longer $R_f$ chain for efficient extraction in the recycling process. Therefore, fluorous borane-sulfides of structural formula (I) having two methylene group spacers (i.e., n=2) are preferred, and an especially preferred embodiment utilizes perfluorinated $R_f$ chains, e.g., perfluorohexyl or perfluorooctyl, as the fluorinated alkyl chain. A perfluorooctyl group provides a fluorous borane-sulfide reagent having about 65%, by weight of the fluorous sulfide, fluorine, when R is methyl.

Preferred fluorous borane-sulfides (I) for use in the hydroboration reaction, therefore, contain one $R_f$ group containing four to ten, and more preferably six to eight, carbon atoms. The $R_f$ group preferably is perfluorinated. In preferred embodiments, the R group is methyl or ethyl, and n is 2.

Important features of the present invention included (a) the facile preparation of crystal-line, odor-free borane-sulfides, e.g., 3,3,4,4,5,5,-6,6,7,7,8,8,9,9,10,10,10-heptadecafluorodecyl methyl sulfide, and its borane complex, hereafter termed fluorous BMS, and its higher and lower homologs, (b) their use in hydroboration and reduction reactions, and (c) their regeneration and recycling using an optional biphasic extraction with an industrial perfluorinated hydrocarbon solvent and a boration using $BH_3$.

Fluorous sulfides (S. Dieng et al., *J. Fluorine Chem.*, 28, pp. 425–440 (1985)) and sulfoxides have been synthesized previously using alternative, longer routes. However, a fluorous borane-sulfide, and its use in a hydroboration or reduction reaction, have not been disclosed. The present invention also is directed to an improved method of synthesizing fluorous sulfides, i.e., compounds having a structure $R_f-(CH_2)_n-S-R$.[17, 18]

After considering (i) the preference for ≧60% fluorine by weight to facilitate regeneration and recycling of the borane-sulfide; (ii) the need for a spacer between the sulfide moiety and the fluorous group to modulate the strongly electron-withdrawing ability of the fluorous group; and (iii) economic considerations, 2-(perfluorooctyl)ethyl methyl sulfide (i.e., Compound 1, 65.4% F) and its corresponding borane adduct Compound 2 (63.6% F) were prepared.

In general, fluorous DMS was readily synthesized from commercial 3,3,4,4,5,5,6,6,7,7,-8,8,9,9,10,10,10-heptadecafluorodecyl iodide by displacement using potassium thioacetate, followed by saponification in the presence of methyl iodide. This synthetic route differs from, and is a considerable improvement over prior syntheses of Compound 1 and homologs of Compound 1. Compound 1 is a colorless, odorless oil.

The passage of borane gas through neat Compound 1 results in the formation of a white solid containing an approximately one-to-one mixture of Compound 1 and Compound 2. This solid mixture then is suspended in FC-72, perfluorohexane, or other fluorous solvent, for use in hydroborations and other reductions. Alternatively, the fluorous suspension of Compound 2 can be generated directly by the passage of borane gas into a fluorous solution of Compound 1.

Hydroborations and reductions using Compound 2 are performed in biphasic mixtures containing a fluorous suspension:of Compound 2 and a solution of the substrate in an appropriate organic solvent, such as dichloromethane. After the reaction is complete, the spent fluorous phase is removed, and the organic phase is subjected to any necessary further treatments and workup standard in the art. For example, in the case of hydroboration, after removal of the spent fluorous solution, the organic layer containing the organoborane compounds is oxidized with alkaline hydrogen peroxide to yield alcohol products. Alternatively, reactions can be conducted in a single organic phase by addition of the solid mixture of Compound 1 and Compound 2. In such instances, the spent fluorous reagent is recovered after the reaction is complete by extraction into a fluorous solvent, such as perfluorohexane.

In particular, the synthesis of Compound 1 was achieved using an improved method, in 76% overall yield, by displacement of iodide from 2-(perfluorooctyl)ethyl iodide using potassium thioacetate, followed by saponification with concomitant alkylation of the thiolate using methyl iodide (Scheme 1). The passage of borane gas, generated from $BF_3 \cdot OEt_2$ and $NaBH_4$,[19] through the neat, liquid sulfide (Compound 1) resulted in the formation of a white solid that was estimated by $^1$H-NMR spectroscopy to be an approximately 1:1 mixture of Compounds 1 and 2.

The $^{11}$B-NMR spectrum of this mixture had a single resonance at δ-22 ppm consistent with the formation of Compound 2. Likewise, the ESI mass spectrum of the mixture demonstrated a molecular ion at m/z 509.3 in full agreement with the formation of Compound 2. Both Compound 1 and the mixture of Compounds 1 and 2 are completely odorless. The solid mixture of Compounds 1 and 2 hydrolyzed slowly on standing in air at room temperature, and additionally showed no tendency to ignite at room temperature. The mixture of Compounds 1 and 2 is stable indefinitely under a nitrogen or argon atmosphere in a refrigerator.

The substantial stability of the solid mixture of Compounds 1 and 2 in air enables this reagent to be weighed on a simple laboratory balance. This, coupled with the ready determination of the stoichiometry of the mixture by integration of the $^1$H-NMR spectrum of the mixture, affords a simple, convenient method of adding precise amounts of the solid mixture to a reaction, which is in contrast to the cumbersome determination of hydrogen released during hydrolysis that typically is used to determine the amount of BMS and similar reagents to be used in a reaction.[20]

The solid mixture of Compounds 1 and 2 contains a high fluorine content, but was only sparingly soluble in the perfluorohydrocarbon FC-72 (i.e., perfluorohexane), with which it typically forms a fine suspension.. The 1:1 mixture is completely soluble in dichloromethane and benzotrifluoride[21] (trifluoromethylbenzene). Either the solid mixture of Compounds 1 and 2, or a suspension in FC-72 or solution in a common organic solvent, can be used in the present methods.

The following reaction scheme illustrates the synthesis of a fluorous sulfide e.g., Compound 1, and a fluorous borane-sulfide complex, e.g., fluorous BMS (Compound 2, wherein $R_f=C_8F_{17}$):

Scheme 1
Preparation of a Fluorous Borane-Sulfide Complex

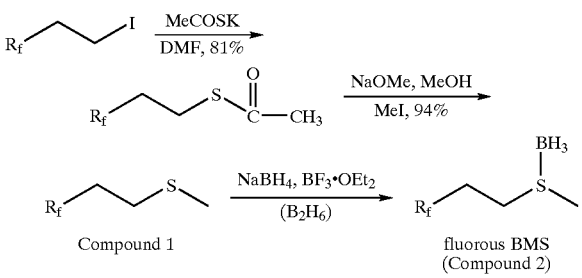

To illustrate the usefulness of a compound of structural formula (I), a series of five hydroborations were conducted using an FC-72 dispersion of the mixture of Compounds 1 and 2 (1.7 M in Compound 2). The test results are set forth in Table 1. These reactions were conducted under a nitrogen blanket in a biphasic mixture of FC-72 and dichloromethane ($CH_2Cl_2$). After consumption of the olefin, the spent fluorous phase was separated from the reaction mixture for recycling, and the organic phase was subjected to oxidative work up using alkaline hydrogen peroxide in a standard manner known to persons skilled in the art. The majority (i.e., about 80%) of Compounds 1 and 2, depleted in Compound 2 because of the hydroboration reaction, was recovered from the FC-72 phase. An additional 10% of Compounds 1 and 2 was recovered from the organic phase following the oxidative work-up and chromatography.

Importantly, no oxidation of the sulfide Compound 1 to a sulfoxide or sulfone was observed under the oxidative work-up conditions.

The recovered Compounds 1 and 2 then were subjected to treatment with borane to regenerate additional Compound 2. The recycled Compound 2 performed exactly the same as a virgin sample of Compound 2.

Of the five examples set forth in Table 1, the first example is a straightforward hydroboration of 2-octene, and oxidative work-up provided a mixture alcohols 4 and 5. The second example is a hydroboration of β-pinene and performs exactly as expected from literature reactions using BMS[4] and borane.[22] The third example, i.e., the hydroboration of a trisubstituted alkene, proceeded in high yield and regio and stereoselectivity, as discussed in the literature.[23] The fourth example shows reaction compatibility with organic functionality,[24] such as found in synthesis of a typical pharmaceutical. The fifth example is an unusual example of hydroboration in the presence of a sulfoxide.[25] The reduced regio-selectivity observed in this example is typical of that seen in BMS hydroborations of other allyl ethers[26] and alkenes substituted with electron-with-drawing groups in general.[27] Compound 2, therefore, functions in hydroboration reactions exactly like BMS, but with important advantages, including a reaction that is odor free, that avoids the generation of dimethyl sulfide, that can be conducted in an organic/fluorous biphasic mixture, and with straightforward regeneration and recycling of Compound 2.

TABLE 1

Hydroboration with Fluorous BMS (2)

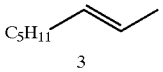

The FC-72 suspension of Compounds 1 and 2, in a biphasic manner with ready regeneration and recycling of Compound 2, also was used to perform a series of other reductions (Table 2). Thus, treatment of a nitroester (15) with the FC-72 dispersion of Compound 2 (in admixture with Compound 1) enabled reduction of the ester group without complications from the nitro group. This result compares to that previously obtained using a $BH_3.THF$ complex.[28] A nitrile (17) also was reduced to a primary amine in a straightforward manner, and N-benzyl-levulinamide (19) was converted to N-benzyl 4-hydroxypentylamine (20), thereby demonstrating the ability of fluorous BMS to reduce both amides and ketones.[6]

pletely odorless. Second the spent FC-72 dispersion, enriched in Compound 1, is readily regenerated by the passage of borane gas to provide regenerated Compound 2. Third, both the solid mixture of Compounds 1 and 2, and its suspension in FC-72, are stable under a nitrogen atmosphere, and show no tendency to ignite in air. Finally, the solid mixture of Compounds 1 and 2 can be readily weighed in air and the reaction stoichiometry determined by standard $^1$H-NMR spectroscopy, thereby permitting facile calculation and use of precise quantities of borane in the reaction. These improvements illustrate that suspensions of Compounds 1 and 2, and similar fluorous borane-sulfide complexes, used as a solid, suspended in a fluoro-carbon

TABLE 2

Further Reductions with Fluorous BMS (2)

| Substrate | Molar equivs of Compound 2 | Products (% yield) | % Recovered Compounds 1/2 |
|---|---|---|---|
| 15 (Ph-CH(NO₂)-CH₂CH₂-CO₂Me) | 1.2 | 16 (83%) (Ph-CH(NO₂)-CH₂CH₂CH₂-OH) | 95 |
| 17 (2-methylbenzyl cyanide) | 1.2 | 18 (81%) (2-methylphenethylamine) | 88 |
| 19 (CH₃-CO-CH₂CH₂-CO-NHBn) | 3 | 20 (79%) (CH₃-CH(OH)-CH₂CH₂CH₂-NHBn) | 86 |

Finally, the ability of Compound 2 to regenerate Corey-type oxaborolidine catalysts[29] in an asymmetric reduction was investigated (Scheme 2). In this reaction, reduction of acetophenone in tetrahydrofuran (THF) using an FC-72 dispersion of Compounds 1 and 2 catalyzed by 10 mol % of catalyst 22 resulted in the formation of (γ)-1-hydroxyethyl-benzene in 94% yield and 84% ee, as determined by chromatography over a Chircel OD column.

Scheme 2

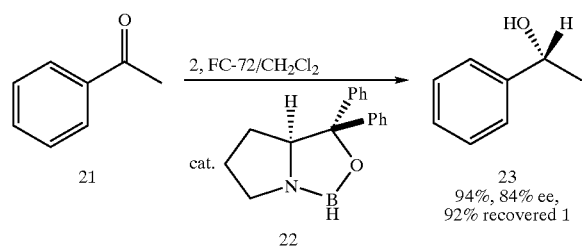

In summary, FC-72 dispersions of Compound 1 and 2 perform in a manner analogous to BMS itself. However, fluorous borane-sulfides of the present reaction provide several important advantages over BMS and similar borane complexes. First, Compound 2 and similar fluorous borane-sulfides, and its reduction product Compound 1, are comsolvent, or used as a solution in a standard organic solvent are suitable for large scale industrial hydroborations and reductions with simple regeneration at a remote borane generation facility.

In particular, given the unstable nature of borane itself, a system is readily envisioned wherein a facility skilled in the art of generating and handling borane generates safe, non-flammable fluorous suspensions of a fluorous borane-sulfide of structural formula (I), then ships the fluorous borane-sulfide to a hydroboration or reduction production facility. After use in a two-phase reactor for example, the spent fluorous solution is returned to the borane facility for regeneration. A further advantage of the solid mixture of Compound 1 and Compound 2 is the ability to weigh the mixture in air, then determine the exact amount of available borane by simple integration of the $^1$H NMR spectrum. Typically, boranes are analyzed by a cumbersome procedure involving controlled hydrolysis under an inert atmosphere with determination of the volume of hydrogen gas released.

As illustrated in Tables 1 and 2, reactions utilizing a fluorous borane-sulfide of the present invention retain the mild conditions and scope of a classic hydroboration reaction in the presence of a wide range of functional groups. The properties that lead to the popularity of the classic hydroboration reaction, therefore, have been retained. In addition to the classic hydroboration of alkenes and alkynes, Tables 1 and 2 show that a reaction using a fluorous borane-sulfide complex is compatible with various functional groups.

An important additional feature of the present invention is recovery of the fluorous sulfide in a high yield, followed by boration to regenerate a fluorous borane-sulfide of structural formula (I).

Fluorinated solvents useful in the hydroboration and reduction reactions in conjunction with the fluorous borane-sulfides of the present invention include, but are not limited to, aliphatic perfluorocarbons containing five to ten carbon atoms and perfluorinated cycloalkanes containing six to ten carbon atoms. Specific examples of fluorinated solvents include, but are not limited to, perfluorohexane, perfluoroheptane, perfluorooctane, perfluorononane, perfluorocyclohexane, perfluoromethylcyclohexane, perfluoro-1,2-dimethylcyclohexane, perfluoro-1,3-dimethylcyclohexane, cis-perfluorodecalin, trans-perfluorodecalin, perfluorokerosene, perfluoromethyldecalin, FC-72, and mixtures thereof.

After recovery of the fluorous sulfide and spent fluorous borane-sulfide, and boration of the recovered material to a fluorous borane-sulfide (I), the recycled fluorous borane-sulfide (I) performed analogously to freshly synthesized fluorous borane-sulfide (I). In fact, a fluorous borane-sulfide (I) was routinely recycled with no attempt to discriminate from virgin material.

The following examples illustrate an efficient method of preparing and using a fluorous borane-sulfide of structural formula (I) in a hydroboration or a reduction reaction. A wide range of alkenes and alkynes can be hydroborated, then oxidized to yield alcohols, in high yield, under completely odor-free reactions. A compound of structural formula (I) also can be used in a variety of reactions to reduce organic functional groups. The fluorous borane-sulfide (I) then is recovered, and regenerated for reuse by a simple boration using $BH_3$.

Experimental Procedures
General

All reagents were purchased from commercial sources and used as received, unless otherwise indicated. Tetrahydrofuran was distilled from sodium/benzophenone ketyl. Methylene chloride was distilled from calcium hydride prior to use. $^1H$, $^{13}C$ and $^{19}F$ NMR spectra were recorded in deuteriochloroform solutions at 500 or 300, 125 or 75, and 282 MHz, respectively. All reactions were performed under a dry nitrogen or argon atmosphere unless otherwise indicated. All hydroboration substrates either were commercially available or prepared as described in the literature. With the exception of Compounds 11, 13, and 14, all hydroboration products were identical to either commercial or literature samples.

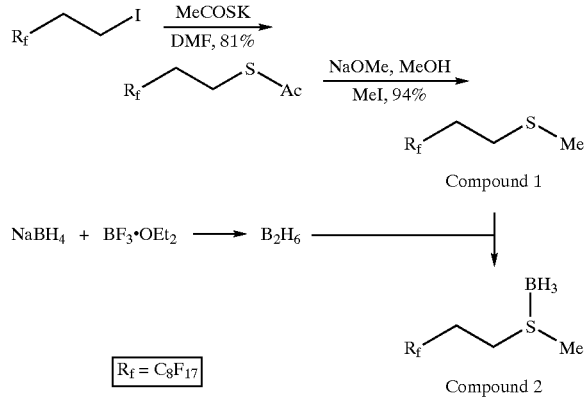

S-[2-(Perflurorooctyl)ethyl] Thioacetate

To a stirred solution of potassium thioacetate (MeCOSK) (1.0 g, 8.75 mmol) in dimethylformamide (DMF) (100 mL) under an argon (Ar) blanket was added pefluorooctylethyl iodide (5.0 g, 8.70 mmol). The resulting mixture was stirred at room temperature for 2 hours. The reaction mixture then was taken up in ether (100 mL) and washed with saturated ammonium chloride ($NH_4Cl$) (30 mL), brine (30 mL), and water (50 mL). Concentration of the organic layer, followed by silica gel chromatography (hexanes:ethyl acetate (EtOAc) 10:1) provided the known thioacetate[1] (3.7 g, 81%) as a very pale yellow oil. $^1H$ NMR δ: 3.11–3.06 (m, 2H), 2.47–2.29 (m, 2H), 2.36 (s, 3H).

3,3,4,4,5,5,6,6,7,7,8,8,9,9,10,10,10-Heptadecafluorodecyl Methyl Sulfide (1)

To the above fluorous thioacetate (3.25 g, 6.20 mmol), dissolved in methanol (MeOH) (40 mL) and cooled to 0° C. under an inert atmosphere, was added a freshly prepared solution of sodium methoxide (NaOMe) (0.33 g, 14.95 mmol) in MeOH (6.3 mL) dropwise. The reaction mixture then was stirred for 0.5 hours before methyl iodide (MeI) (2.1 g, 14.8 mmol) dissolved in MeOH (5 mL) was added dropwise over a period of 10 minutes at 0° C. After stirring at room temperature for one hour the reaction mixture was poured into cold water and extracted with ether. Concentration of the ether layer followed by silica gel chromatography (hexanes:EtOAc 40:1) yielded the fluorous sulfide Compound 1 (2.9 g, 94%) as a colorless oil. $^1H$ NMR δ: 2.74–2.69 (m, 2H), 2.47–2.33 (m, 2H), 2.16 (s, 3H). $^{13}C$ NMR δ: 120.2–104.6 (m), 31.8 (t), 24.8 (t), 15.5 (s). $^{19}F$ NMR δ: −8.3 (t), −41.9 (t), −49.3, −49.4, −49.5, −50.3, −51.0, −3.7. ESIMS Calcd. For $C_{11}H_7F_{17}S$ $[M-H]_+$:493.1. Found 493.1.

Solid Mixture of Fluorous Sulfide (1) and Fluorous Borane-Sulfide (2)

Diborane gas ($B_2H_6$), generated by reacting sodium borohydride ($NaBH_4$) (1.5 g, 39.0 mmol) in diglyme (12 mL) with $BF_3.Et_2O$ (6 mL) was passed through the neat fluorous sulfide (1) (2.9 g, 5.88 mmol) at 25° C. for a period of 10 minutes, after which the oily fluorous sulfide was converted into a white solid. $^1H$ NMR spectroscopy showed a 1:1 relation of Compounds 2:1 (coordinated:noncoordinated) and $^{11}B$ NMR showed a single resonance at −22.0 ppm corresponding to Compound 2. ESIMS Calcd. For $C_{11}H_{10}BF_{17}S$ $[M+H]_+$:509.0. Found 509.3. An $^1H$ NMR spectrum of the mixture showed the above resonances for Compound 1 and the following resonances for Compound 2: δ 2.89–2.83 (m, 1H), 2.77–2.71 (m, 1H), 2.62 (m, 2H), 2.35 (s, 3H).

Typical Procedure for the Hydroboration of Alkenes with the Mixture of Compounds 1 and 2

To alkene 12 of Table 1 (0.15 g, 0.32 mmol) dissolved in a biphasic solvent system of methylene chloride ($CH_2Cl_2$) (2 mL) and FC-72 (2 mL) under argon was added the 1/1 mixture of Compounds 1 and 2 (0.1 g, 0.1 mmol of Compound 2) at 0° C., followed by stirring for one hour. The FC-72 layer then was removed, and the organic layer oxidized by adding 3 M sodium hydroxide (NaOH) (0.035 mL, 0.105 mmol) and 30% hydrogen peroxide ($H_2O_2$) (0.019 mL, 0.165 mmol), followed by stirring overnight. Evaporation of the FC-72 phase provided Compound 1 (0.08 g, 80%). The $CH_2Cl_2$ layer was diluted with water (2 mL), and stirred for 0.5 hour. Evaporation of the $CH_2Cl_2$, followed by column chromatography (hexanes:EtOAc 40:1→3:1) gave the fluorous sulfide Compound 1 (0.01 g, 10%), followed by the alcohols 13 (0.087 g, 59%) and 14 (0.029 g, 19%) of Table 1 in a 3:1 ratio. Alcohol 13:$^1H$ NMR δ: 7.50–7.26 (m, 10H), 5.62 (s, 1H), 4.89 (d, J=11.7 Hz, 1H), 4.75 (d, J=11.7 Hz, 1H), 4.61 (d, J=1.2 Hz, 1H), 4.33 (dd, J=3.6, 1.2 Hz, 1H), 4.25–4.16 (m, 2H), 4.09 (dd, J=9.7, 3.6 Hz, 1H), 3.93–3.88 (m, 1H), 3.83–3.66 (m, 5H), 3.01–2.94 (m, 1H), 2.74–2.67 (m, 1H), 2.60 (br.s, 1H), 1.84–1.80 (m, 2H), 1.39 (t, J=7.5 Hz, 3H); $^{13}C$ NMR δ: 137.7, 137.2, 129.2, 128.6, 128.4, 128.2, 128.1, 126.1, 101.8, 92.5, 78.2, 75.8, 74.4, 73.9, 71.0, 70.1, 68.2, 60.9, 44.1, 32.2, 6.1.

Alcohol 14 ¹H NMR (14) δ: 7.48–7.26 (m, 10H), 5.63 (s, 1H), 4.89 (dd, J=11.55, 5.1 Hz, 1H), 4.77 (d, J=12 Hz, 1H), 4.58 (s, 1H), 4.41–3.99 (m, 5 H), 3.84–3.57 (m, 3 H), 3.47–3.29 (m, 1H), 2.99–2.94 (m, 1H), 2.74–2.67 (m, 1H), 1.40 (t, J=7.5 Hz, 3H), 1.10 (d, J=6.9 Hz, 3H); ¹³C NMR δ: 137.5, 137.1, 129.3, 128.6, 128.4, 128.2, 128.1, 126.1, 101.8, 92.6, 78.9, 78.3, 76.3, 75.3, 73.9, 70.0, 68.2, 67.2, 64.7, 44.2, 18.2, 6.0.

(+)-(2S,3aR,8aS)-3a-(3-Hydroxypropyl)-1,2-bismethoxycarbonyl-8-phenylsulfonyl-1,2,3,3a,8,8a-hexahydropyrrolo[2,3b] indole Compound 11 from Table 1 was prepared generally as alcohols 13 and 14. ¹H NMR δ: (50° C.) 7.97 (d, J=6.9, 3.9 Hz, 2H), 7.55–7.46 (m, 3H), 7.30 (d, J=8.1 Hz, 1H), 7.26–7.19 (m, 1H), 7.08–7.04 (m, 2H), 6.06 (s, 1H), 4.64 (d, J=9.0 Hz, 1H), 3.49 (t, J=6.0 Hz, 2H), 3.35 (br.s, 3H), 3.18 (s, 3H), 2.68 (d, J=12.9 Hz, 1H), 2.35 (dd, J=12.9, 9.3 Hz, 1H), 1.68–1.58 (m, 3H), 1.43 (br.s, 1H), 1.41–1.36 (m, 1H); ¹³C NMR δ: 171.2, 154.6, 142.8, 134.2, 132.7, 129.3, 129.2, 125.7, 124.4, 124.1, 116.7, 83.4, 62.6, 59.8, 52.3, 52.2, 39.4, 34.8, 27.7. [α]$_D$=+23° (c=1.1 g/100 mL CHCl$_3$)

Typical Procedure for the Reduction of Esters Using the Mixture of Compounds 1 and 2

To ester 15 of Table 2 (0.036 g, 0.162 mmol) dissolved in a biphasic system containing THF (1 mL) and FC-72 (1 mL) was added the 1/1 mixture of Compounds 1 and 2 (0.19 g, 0.19 mmol of Compound 2), followed by stirring for 18 hours. After completion of the reaction, MeOH (0.5 mL) was added to quench excess borane. The FC-72 layer was evaporated to provide Compound 1 (0.16 g, 84%). The organic layer was concentrated and purified by silica gel column chromatography (hexanes:EtOAc 40:1→3:1) to yield Compound 1 (0.02 g, 11%) followed by the alcohol 16 of Table 2 (0.03 g, 95%).

Typical Procedure for the Reduction of Nitriles Using the Mixture of Compounds 1 and 2

To nitrile 17 of Table 2 (0.02 g, 0.15 mmol) dissolved in THF (1 mL) was added the 1/1 mixture of Compounds 1 and 2 (0.18 g, 0.18 mmol of 2), followed by refluxing for 3 hours. The reaction mixture then was cooled to room temperature, and 6 N hydrochloric acid (HCl) (0.09 mL, 0.54 mmol) was added dropwise. The reaction mixture then was heated under reflux for 0.5 hour. The resulting clear solution was cooled to 0° C., and FC-72 (1 mL) was added followed by stirring for another 60 minutes. The FC-72 then was removed, and evaporated to provide Compound 1 (0.13 g, 78%). The organic-aqueous reaction mixture then was basified with 3 M NaOH (0.30 mL, 0.90 mmol), and the liberated amine extracted with ether (5 mL). Concentration of the ether layer followed by column chromatography on silica gel (hexanes:EtOAc 40:1→25:1) yielded fluorous sulfide Compound 1 (0.02 g, 10%) followed by the amine 18 of Table 2 (0.016 g, 81%).

Typical Procedure for the Reduction of Amides Using the Mixture of Compounds 1 and 2

To amide 19 of Table 2 (0.03 g, 0.14 mmol) dissolved in a THF (1 mL) and FC-72 (1 mL) biphasic system was added the 1/1 mixture of Compounds 1 and 2 (0.42 g, 0.42 mmol of 2), followed by refluxing for 4 hours. The reaction mixture then was cooled, and the FC-72 layer evaporated to yield Compound 1 (0.33 g, 78%). Methanol (0.5 mL) was added to the organic layer, which then was refluxed for 0.5 hour. The organic layer then was concentrated, and purified by flash column chromatography on silica gel (hexanes:EtOAc 40:1→1:20) to yield the fluorous sulfide Compound 1 (0.03 g, 8%) followed by amine 20 of Table 2 (0.021 g, 79%).

Typical Procedure for the Oxaborolidine Catalyzed Reduction of Ketones with the Mixture of Compounds 1 and 2

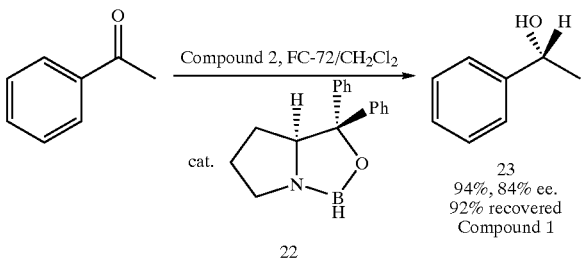

23
94%, 84% ee.
92% recovered
Compound 1

To Compound 22 (0.004 g, 0.0150 mmol) dissolved in a biphasic system containing THF (0.5 mL) and FC-72 (0.5 mL) was added the 1/1 mixture of Compounds 1 and 2 (0.30 g, 0.30 mmol of 2), followed by stirring at 45° C. overnight. Acetophenone (0.018 g, 0.150 mmol) then was added dropwise over a period of 30 minutes. After stirring for an additional 30 minutes, the reaction mixture was quenched with MeOH (0.3 mL). The FC-72 layer was separated from the reaction mixture, and the organic layer then was stirred with additional FC-72 (1 mL). The FC-72 layers were combined and concentrated to provide Compound 1 (0.24 g, 80%). The organic layer was concentrated and purified by column chromatography on silica gel (hexanes:EtOAc 40:1→1:20) to provide fluorous sulfide Compound 1 (0.04 g, 12%) followed by (R)-(+)-1-phenylethanol (23) (0.017 g, 94%). [α]$_D$=+40° (c=0.4 g/100 mL CH$_2$Cl$_2$), 84% ee. See C. Naud et al., Fluorine Chem., 104, pp. 173–184 (2000).

The present invention, therefore, is directed to an efficient method of preparing fluorous sulfides and their boration to the corresponding fluorous borane-sulfides. The fluorous borane-sulfides hydroborate a variety of alkenes and alkynes, and reduce a variety of organic functional groups, to provide desired products in excellent yield. Undesired products are avoided by use of the fluorous borane-sulfides of structural formula (I), and noxious by-products are not generated. The fluorous sulfide is efficiently recovered for reuse by a simple extraction and evaporation of the fluorinated solvent, followed by boration to regenerate the fluorous borane-sulfide for recycling. The entire hydroboration and reduction processes are odor free and suitable for industrial scale oxidations.

References (1) H. C. Brown et al., J. Am. Chem. Soc., 92, 1637–1646 (1970).
(2) M. Zaidlewicz et al., In EROS; L. A. Paquette,. Ed.; Wiley: Chichester, Vol. 1; pp. 638–644 (1995).
(3) L. M. Braun et al., J. Org. Chem., 36, 2388–2389 (1971).
(4) C. F. Lane, J. Org. Chem., 39, 1437–1438 (1974).
(5) H. C. Brown et al., J. Org. Chem., 42, 1392–1398 (1977).
(6) M. Zaidlewicz, In EROS; L. A. Paquette, Ed.; Wiley: Chicester, Vol. 1; pp. 634–637 (1995).
(7) H. C. Brown et al., J. Org. Chem., 57, 4970–4976 (1992).
(8) H. C. Brown et al., J. Org. Chem., 66, 4795–4798 (2001).
(9) M. Follet, Chem. Ind., 123–128 (1986).
(10) I. T. Horvath, Acc. Chem. Res., 31, 641–650 (1998).
(11) D. P. Curran, Angew. Chem. Int. Ed. Engl., 37, 1174–1196 (1998).
(12) D. P. Curran et al., Tetrahedron, 58, 3823–3825 (2002).
(13) D. Crich et al., Tetrahedron, 55, 14261–14268 (1999).
(14) D. Crich et al., Org. Lett., 1, 269–272 (1999).
(15) D. Crich et al., Org. Lett., 2, 989–991 (2000).
(16) D. Crich et al., Org. Lett., 2, 4029–4031 (2000).
(17) D. Crich et al., J. Am. Chem. Soc., 123, 7449–7450 (2001).
(18) D. Crich, Tetrahedron, 58, 3865–3870 (2002).

(19) G. Zweifel et al., *Org. React.,* 13, 1–54 (1963).
(20) H. C. Brown, *Organic Synthesis via Boranes;* Wiley: New York, 1975.
(21) A. Ogawa et al., *J. Org. Chem.,* 62, 450–451 (1997).
(22) G. W. Zweifel et al., *J. Am. Chem. Soc.,* 86, 393–397 (1964).
(23) H. C. Brown et al., G. *J. Am. Chem. Soc.,* 83, 2544–2551 (1961).
(24) M. Bruncko et al., *J. Org. Chem.,* 59, 5543–5549 (1994).
(25) D. Crich et al., *Tetrahedron,* 55, 1569–1580 (1999).
(26) J. E. T. Corrie et al., *J. Chem. Soc., Perkin Trans. 1,* 1583–1592 (1996).
(27) K. Smith et al., In *Comprehensive Organic Synthesis;* Trost, B. M. Ed.; Pergamon Press: Oxford, Vol. 8; pp. 2573–2575 (1991).
(28) D. Crich et al., *Org. Lett.,* 4, 0000–0000 (2002).
(29) E. J. Corey et al., *Angew. Chem. Int. Ed. Engl.,* 37, 1987–2012 (1998).

Obviously, many modifications and variations of the invention as hereinbefore set forth can be made without departing from the spirit and scope thereof, and, therefore, only such limitations should be imposed as are indicated by the appended claims.

What is claimed is:

1. A fluorous borane-sulfide having a structure

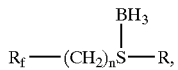

wherein $R_f$ is a fluorinated hydrocarbon chain containing one to twelve carbon atoms; R is $C_{1-4}$alkyl or $(CH_2)_n$—$R_f$; and n is 1 to 3.

2. The borane-sulfide of claim 1 wherein $R_f$ contains four to ten carbon atoms.

3. The borane-sulfide of claim 1 wherein $R_f$ contains six to eight carbon atoms.

4. The borane-sulfide of claim 1 wherein $R_f$ is perfluorinated.

5. The borane-sulfide of claim 1 wherein the fluorous sulfide $R_f$—$(CH_2)_n$S—R contains at least 35%, by weight, fluorine.

6. The borane-sulfide of claim 1 wherein the fluorous sulfide $R_f$—$(CH_2)_n$S—R contains at least 35% to about 70%, by weight, fluorine.

7. The borane-sulfide of claim 1 wherein R is methyl or ethyl.

8. The borane-sulfide of claim 1 wherein n is 2.

9. The borane-sulfide of claim 1 wherein $R_f$ is $C_6F_{13}$ or $C_8F_{17}$.

10. The borane-sulfide of claim 1 having a structure

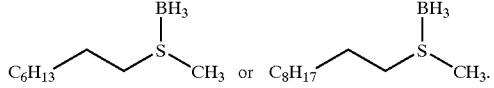

11. A method of hydroborating an alkene or an alkyne comprising reacting the alkene or alkyne with a fluorous borane-sulfide having a structure

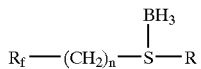

wherein $R_f$ is a fluorinated hydrocarbon chain containing one to twelve carbon atoms; R is $C_{1-4}$alkyl or $(CH_2)_n$—$R_f$; and n is 1 to 3.

12. The method of claim 11 wherein the hydroboration is performed in the presence of a fluorous sulfide having a structure $R_f$—$(CH_2)_n$—S—R, wherein $R_f$ is a fluorinated hydrocarbon chain containing one to twelve carbon atoms; R is $C_{1-4}$alkyl or $(CH_2)_n$-$R_f$; and n is 1 to 3.

13. The method of claim 11 wherein $R_f$ is perfluorinated.

14. The method of claim 11 wherein $R_f$ is $C_6F_{13}$ or $C_8F_{17}$.

15. The method of claim 11 wherein the fluorous borane-sulfide is

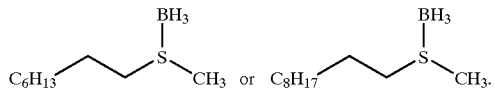

16. The method of claim 11 wherein the hydroboration is performed in a solvent comprising a fluorinated hydrocarbon.

17. The method of claim 16 wherein the solvent further comprises a second solvent that is immiscible with the fluorinated hydrocarbon.

18. The method of claim 16 wherein the fluorinated hydrocarbon is selected from the group consisting of perfluorohexane, perfluoroheptane, perfluorooctane, perfluorononane, perfluorocyclohexane, perfluoromethylcyclohexane, perfluoro-1,2-dimethylcyclohexane, perfluoro-1,3-dimethylcyclohexane, cis-perfluorodecalin, trans-perfluorodecalin, perfluorokerosene, perfluoromethyldecalin, and mixtures thereof.

19. The method of claim 11 comprising further steps wherein a sulfide by-product of the hydroboration reaction having a formula $R_f$($CH_2$)$_n$—S—R is separated from the reaction mixture, then reacted with $BH_3$ to regenerate

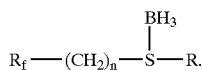

20. The method of claim 11 comprising further steps wherein the hydroboration alkene or alkyne is treated with a base and an oxidizing agent to provide an alcohol corresponding to the alkene or alkyne.

21. The method of claim 20 wherein the oxidizing agent is hydrogen peroxide.

22. A method of reducing a reducible organic functionality of a compound comprising reacting the functionality with a fluorous borane-sulfide having a structure

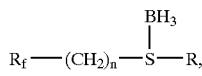

wherein $R_f$ is a fluorinated hydrocarbon chain containing one to twelve carbon atoms; R is $C_{1-4}$alkyl or $(CH_2)_n$-$R_f$; and n is 1 to 3.

23. The method of claim 22 wherein the organic functionality is selected from the group consisting of cyano, amido, acyloxy, and keto.

24. The method of claim 22 comprising further steps wherein a fluorous sulfide by-product of the reduction having a formula $R_f$—$(CH_2)_n$—S—R is separated from the reaction mixture, then reacted with $BH_3$ to regenerate

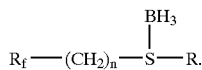

* * * * *

UNITED STATES PATENT AND TRADEMARK OFFICE
CERTIFICATE OF CORRECTION

PATENT NO. : 6,849,767 B2
DATED : February 1, 2005
INVENTOR(S) : David C. Crich et al.

It is certified that error appears in the above-identified patent and that said Letters Patent is hereby corrected as shown below:

Column 15,
Line 55, "$C_6H_{13}$" should be -- $C_6F_{13}$ -- and "$C_8H_{17}$" should be -- $C_8F_{17}$ --

Column 16,
Line "$C_6H_{13}$" should be -- $C_6F_{13}$ -- and "$C_8H_{17}$" should be -- $C_8F_{17}$ --
Line 39, "hydroboration" should be -- hydroborated --

Signed and Sealed this

Nineteenth Day of July, 2005

JON W. DUDAS
*Director of the United States Patent and Trademark Office*